United States Patent [19]
Vértesy et al.

[11] Patent Number: 5,939,399
[45] Date of Patent: Aug. 17, 1999

[54] POLYENE ANTIBIOTICS, 3874 H1 TO H6, PROCESSES FOR THEIR PREPARATION AND USE

[75] Inventors: Laszló Vértesy, Eppstein; Michael Kurz, Hofheim; Joachim Wink, Rödermark; Astrid Markus, Liederbach; Wilhelm Stahl, Idstein, all of Germany

[73] Assignee: Hoechst Aktiengesellschaft, Frankfurt am Main, Germany

[21] Appl. No.: 08/914,652

[22] Filed: Aug. 19, 1997

[30] Foreign Application Priority Data

Aug. 19, 1996 [DE] Germany .................. 196 33 310
Nov. 28, 1996 [DE] Germany .................. 196 49 349

[51] Int. Cl.$^6$ .............. A61K 31/70; C07H 17/04; C07G 11/00; C12P 19/46
[52] U.S. Cl. .............. 514/31; 435/84; 435/886; 435/892; 536/6.5; 536/16.8; 536/18.7
[58] Field of Search .............. 514/31; 536/6.5, 536/16.8, 18.7

[56] References Cited

U.S. PATENT DOCUMENTS 4,027,015  5/1977  Weinstein et al. .............. 424/119
4,272,525  6/1981  Wright .............. 514/8

FOREIGN PATENT DOCUMENTS 0 010 297  4/1980  European Pat. Off. .
0 489 308  6/1992  European Pat. Off. .

OTHER PUBLICATIONS

"Amphotericin B", The Merck Index, 11th edition, p. 93, (1989).
Remington's Pharmaceutical Sciences, 17th edition, Chapter 76., p. 1418, (1985).

*Primary Examiner*—Alan L. Rotman
*Attorney, Agent, or Firm*—Finnegan, Henderson, Farabow, Garrett & Dunner, L.L.P.

[57] ABSTRACT

Novel polyene antibiotics, 3874 H1 to H6, processes for their preparation and use which are suitable for treating fungal diseases, trichomonad diseases, and for treating diseases associated with an increased steroid concentration.

8 Claims, No Drawings

POLYENE ANTIBIOTICS, 3874 H1 TO H6, PROCESSES FOR THEIR PREPARATION AND USE

BACKGROUND OF THE INVENTION

The present invention relates to novel heptaene antibiotics, processes for their preparation and their use.

A large number of heptaene antibiotics has already been described. Heptaene antibiotics are macrocyclic lactones comprising as characteristic feature 7 double bonds conjugated together. They are natural substances which are obtained from microbes and are used as antimycotics, as antitrichomonal agents or as agents for binding steroids (cholesterol). However, some of them are very toxic compounds which, for this reason, are not used systemically (injected), except for the commercial product amphotericin B (The Merck Index, eleventh edition, 1989, page 93), the prototype of polyene antibiotics. Because of the increase in fungal diseases, there continues to be a great need for novel antifungal antibiotics which are either more effective or better tolerated than known polyene antibiotics.

It has now been found, surprisingly, that Streptomyces spec. HAG 3874, DSM 11007, is able to produce novel, highly active heptaene antibiotics which not only are very effective but in some cases are also well tolerated.

SUMMARY OF THE INVENTION

The invention accordingly relates to the compounds 3874 H1–H6 and to their physiologically tolerated salts and their obvious chemical equivalents.

3874 H1, molecular formula: $C_{58}H_{86}N_2O_{18}$, MW 1099.3

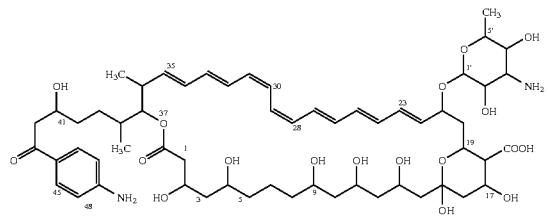

3874 H2, molecular formula: $C_{59}H_{88}N_2O_{18}$, MW 1113.3

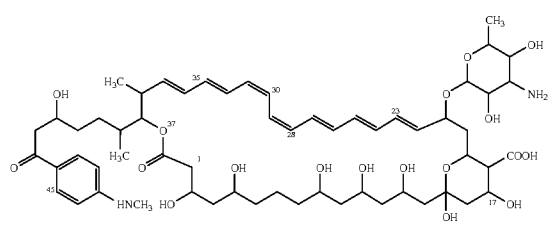

3874 H3, Molecular formula: $C_{57}H_{87}NO_{18}$, MW 1074.3

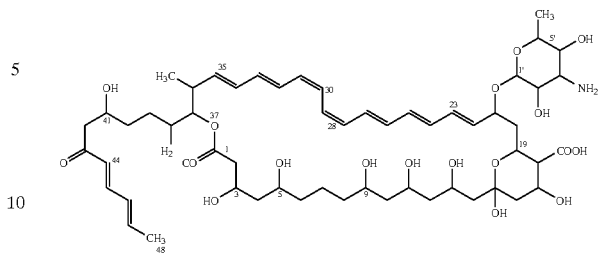

3874 H4, molecular formula: $C_{58}H_{84}N_2O_{18}$, MW 1097.3
3874 H5, molecular formula: $C_{59}H_{86}N_2O_{18}$, MW 1111.3
3874 H6, molecular formula: $C_{57}H_{85}NO_{18}$, MW 1072.3.

The antibiotics 3874 H1 to H6 differ from substances disclosed in the literature owing to the indicated structural and molecular formulae and the two cis double bonds in the Δ28/29 and Δ30/31 position, which are the same in all the compounds according to the invention. The compounds according to the invention have characteristic ultraviolet spectra.

The present invention furthermore relates to the processes for preparing said compounds. One process for preparing said compounds comprises cultivating the microorganism Streptomyces species HAG 3874 (DSM 11007) in an aqueous nutrient medium, and subsequently isolating and purifying the target compounds. Said microorganism was deposited on Jun. 21, 1996, under the provisions of the Budapest treaty at the Deutsche Sammlung von Mikroorganismen und Zelikulturen, Mascheroder Weg 1b, D-38124 Braunschweig under the number DSM 11007.

DESCRIPTION OF THE PREFERRED EMBODIMENTS

Streptomyces spec. DSM 11007 has white aerial mycelium and gray spore chains. It forms the spore chains characteristic of Streptomyces. In a nutrient solution which contains a source of carbon and a source of nitrogen, plus the usual inorganic salts, Streptomyces spec. DSM 11007 produces the compound 3874 H1 to H6.

It is also possible to employ in place of the strain DSM 11007 its mutants and variants as long as they synthesize the compounds according to the invention. Such mutants can be produced in a manner known per se by physical means, for example irradiation such as with ultraviolet or X-rays, or chemical mutagens such as, for example, ethyl methanesulfonate (EMS); 2-hydroxy4-methoxybenzophenone (MOB) or N-methyl-N'-nitro-N-nitrosoguanidine (MNNG).

Screening for mutants and variants which produce the antibiotics according to the invention can take place by determining the biological activity of the active substances accumulated in the culture broth, for example by testing the antimycotic action by the method described below.

Suitable and preferred as source of carbon for the aerobic fermentation are assimilable carbohydrates and sugar alcohols, such as glucose, lactose or D-mannitol, and carbohydrate-containing natural products such as, for example, malt extract. Suitable nitrogenous nutrients are: amino acids, peptides and proteins, and their degradation products such as peptones or tryptones, also meat extracts, milled seeds, for example of corn, wheat, beans, soybean or the cotton plant, distillation residues from the production of alcohol, meat meals or yeast extracts, but also ammonium salts and nitrates. Inorganic salts which the nutrient solution may contain are, for example, chlorides, carbonates, sulfates or phosphates of the alkali metals or alkaline earth metals, iron, zinc, cobalt and manganese.

Production of the heptaenes 3874 H1 to H6 takes place particularly well in, for example, a nutrient solution which contains about 0.5 to 5% glucose, preferably 1 to 2%, 0.5 to 5% soybean meal, preferably 1 to 2%, cornsteep, preferably 0.2 to 1%, 0.05 to 1.0% $CaCO_3$, preferably 0.1 to 0.5% and 0.1 to 2% NaCl, preferably 0.2 to 1%, in each case based on the weight of the complete nutrient solution.

Cultivation takes place aerobically, that is to say, for example, submerged with shaking or stirring in shaken flasks or fermenters, where appropriate introducing air or oxygen. The fermentation can be carried out, for example, in wide-neck bottles or round-bottom flasks with various volumes, in glass fermenters or stainless steel tanks. It can be carried out at a temperature in the range from about 20 to 35° C., preferably at about 25 to 30° C. The pH should be between 4 and 10, advantageously between 5.5 and 8.5. The microorganism is generally cultivated under these conditions for a period of from 20 to 300 hours, preferably 24 to 140 hours. Cultivation advantageously takes place in several stages, i.e. initially one or more precultures are prepared in a liquid nutrient medium and then transferred into the actual production medium, the main culture, for example in the ratio 1:10 by volume. The preculture is obtained, for example, by transferring a sporulated mycelium into a nutrient solution and allowing it to grow for about 20 to 120 hours, preferably 24 to 72 hours. The sporulated mycelium can be obtained, for example, by allowing the strain to grow on a solid or liquid nutrient medium, for example yeast-malt agar or potato-dextrose agar, for about 1 to 40 days, preferably 3 to 10 days.

The progress of the fermentation and the production of the antibiotics 3874 H1 to H6 can be followed by methods known to the skilled worker, such as, for example, by testing the biological activity in bioassays or by chromatographic methods such as thin-layer chromatography (TLC) or high performance liquid chromatography (HPLC).

It is characteristic of the strain HAG 3874 (DSM 11007) that it is able to produce carbazomycin B und pimprinin, which are antibiotics known from the literature, besides the heptaenes.

The antibiotics 3874 H1 to H6 may occur both in the mycelium and in the culture filtrate, with the major quantity normally being found in the biomass (mycelium). It is therefore expedient to separate the latter from the filtrate by filtration or centrifugation. The filtrate is extracted with a solvent which is immiscible with water, such as, for example, 1-butanol, ethyl acetate, chloroform or the like. The mycelium is expediently extracted with methanol or acetone, but the abovementioned salts which are immiscible with water can also be used.

The extractions can be carried out in a wide pH range, but it is expedient to operate in a neutral medium, preferably between pH 5 and pH 9. The organic extracts can be concentrated and dried in vacuo, for example.

One method for isolating the heptaenes 3874 H1 to H6 is solution partition in a manner known per se.

Another purification method is chromatography on adsorption resins such as, for example, on DIAION® HP-20 (Mitsubishi Casei Corp., Tokyo), on AMBERLITE® XAD 7 (Rohm and Haas, U.S.A.), on AMBERCHROM® CG, (Toso Haas, Philadelphia, U.S.A.) or the like. The separations can be carried out in a wide pH range. The range pH 1 to pH 13 is preferred; and the range pH 2 to pH 12 is particularly preferred. Also suitable are numerous reverse phase supports, for example $RP_{18}$, as have become generally known, for example in the field of high pressure liquid chromatography (HPLC).

Another possibility for purifying the antibiotics according to the invention is to use so-called normal phase chromatography supports such as, for example, silica gel or $Al_2O_3$ or others in a manner known per se. Suitable for this purpose are many solutions and their mixtures, such as, for example, chloroform/methanol mixtures to which basic solvents such as, for example, pyridine have been added.

An alternative isolation method is to use molecular sieves such as, for example, FRACTOGEL® TSK HW-40, SEPHADEX® LH-20 and others, in a manner known per se. It is furthermore also possible to isolate the heptaenes by crystallization from enriched material. Suitable for this purpose are, for example, organic solvents and their mixtures, anhydrous or with added water. An additional method for isolating and purifying the antibiotics according to the invention comprises the use of anionic exchangers, preferably in the pH range from 7 to 10 and cation exchangers preferably in the pH range from 3 to 7. It is particularly suitable to use for this purpose buffer solutions to which proportions of organic solvents have been added.

The antibiotics 3874 H1 to H6 or chemical derivatives thereof can be converted by methods known to the skilled worker into the corresponding pharmacologically suitable salts.

Obvious chemical equivalents of the compounds according to the invention are compounds which have a slight chemical difference, that is to say have the same activity, or are converted under mild conditions into the compounds according to the invention. Said equivalents include, for example, esters, amino derivatives, complexes or adducts of or with the compounds according to the invention.

Pharmacologically suitable salts of the compounds according to the invention mean both inorganic and organic salts as described in Remington's Pharmaceutical Sciences (17th edition, page 1418 (1985)). Particularly suitable salts are alkali metal, ammonium and alkaline earth metal salts, salts with physiologically tolerated amines and salts with inorganic or organic acids such as, for example, HCl, HBr, $H_2SO_4$, maleic acid and fumaric acid.

The physicochemical and spectroscopic properties of the antibiotics according to the invention may be summarized as follows:

3874 H1

Appearance: greenish yellow substance soluble in methanol, acetonitrile and chloroform. Stable in neutral and weakly alkaline medium but unstable in acidic and strongly alkaline solution and on exposure to light, heat and oxygen.

Molecular formula: $C_{58}H_{86}N_2O_{18}$
Molecular weight: 1099.3
$^1$H-NMR: see Table 1
UV maxima (log ε): 232 nm (4.49), 286 nm (4.32), 338 nm (4.64), 357 nm (4.86), 377 nm (5.00), 398 nm (4.98)

3874 H2

Appearance: greenish yellow substance soluble in methanol, acetonitrile and chloroform. Stable in neutral and weakly alkaline medium but unstable in acidic and strongly alkaline solution and on exposure to light, heat and oxygen.

Molecular formula: $C_{59}H_{88}N_2O_{18}$
Molecular weight: 1113.3
UV maxima (log ε): 232 nm (4.49), 286 nm (4.32), 338 nm (4.64), 357 nm (4.86), 377 nm (5.00), 398 nm (4.98)

3874 H3

Appearance: greenish yellow substance soluble in methanol and other lower alcohols, acetonitrile and chloroform. Stable in neutral and weakly alkaline medium but unstable in acidic and strongly alkaline solution and on exposure to light, heat and oxygen.

Molecular formula: $C_{57}H_{87}NO_{13}$
Molecular weight: 1074.3
$^1$H-NMR: see Table 1
UV maxima (log ε): 233 nm (4.39), 241 nm (4.39), 249 nm (4.28), 275 nm (4.41), 341 nm (4.54), 358 nm (4.82), 378 nm (5.00), 399 nm (4.94).

3874 H4

Appearance: greenish yellow substance soluble in methanol, acetonitrile and chloroform. Stable in neutral and weakly alkaline medium but unstable in acidic and strongly alkaline solution and on exposure to light, heat and oxygen.

Molecular formula: $C_{58}H_{84}N_2O_{18}$
Molecular weight: 1097.3
UV maxima (log ε): 232 nm (4.49), 286 nm (4.32), 338 nm (4.64), 357 nm (4.86), 377 nm (5.00), 398 nm (4.98)

3874 H5

Appearance: greenish yellow substance soluble in methanol, acetonitrile and chloroform. Stable in neutral and weakly alkaline medium but unstable in acidic and strongly alkaline solution and on exposure to light, heat and oxygen.

Molecular formula: $C_{59}H_{86}N_2O_{18}$
Molecular weight: 1111.3
UV maxima (log ε): 232 nm (4.49), 286 nm (4.32), 338 nm (4.64), 357 nm (4.86), 377 nm (5.00), 398 nm (4.98)

3874 H6

Appearance: greenish yellow substance soluble in methanol and other lower alcohols, acetonitrile and chloroform. Stable in neutral and weakly alkaline medium but unstable in acidic and strongly alkaline solution and on exposure to light, heat and oxygen.

Molecular formula: $C_{57}H_{85}NO_{13}$
Molecular weight: 1072.3
$^1$H-NMR: see Table 1
UV maxima (log ε): 233 nm (4.39), 241 nm (4.39), 249 nm (4.28), 275 nm (4.41), 233 nm (4.39), 341 nm (4.54), 358 nm (4.82), 378 nm (5.00), 399 nm (4.94).

The good solubility means that the antibiotics according to the invention differ advantageously from amphotericin B which has only very low solubility in the said solvents and others, and thus creates great problems on use.

TABLE 1

Chemical shifts in the $^1$H-NMR spectra of 3874 H3 and 3874 H1 recorded in deuteromethanol at 17° C.

| Position on C atom | 3874 H3 | 3874 H1 | Position on C atom | 3874 H3 | 3874 H1 |
|---|---|---|---|---|---|
| 1 | — | — | 29 | 6.61 | 6.61 |
| 2 | 2.49/2.14 | 2.45/2.15 | 30 | 6.51 | 6.51 |
| 3 | 4.28 | 4.28 | 31 | 6.06 | 6.06 |
| 4 | 1.66/1.41 | 1.66/1.41 | 32 | 6.82 | 6.82 |
| 5 | 3.36 | 3.37 | 33 | 6.22 | 6.20 |
| 6 | 1.30 | 1.30 | 34 | 6.19 | 6.20 |
| 7 | 1.84/1.12 | 1.85/1.11 | 35 | 5.38 | 5.38 |
| 8 | 1.31 | 1.30 | 36 | 2.48 | 2.48 |
| 9 | 3.69 | 3.70 | 36-Me | 1.02 | 1.02 |
| 10 | 1.44 | 1.43 | 37 | 4.76 | 4.77 |
| 11 | 4.04 | 4.05 | 38 | 1.85 | 1.86 |
| 12 | 1.52/1.25 | 1.51/1.38 | 38-Me | 0.98 | 0.98 |
| 13 | 4.43 | 4.42 | 39 | 1.36 | 1.40 |
| 14 | 1.72/1.56 | 1.72/1.55 | 40 | 1.58/1.46 | 1.62/1.51 |
| 15 | — | — | 41 | 3.97 | 4.06 |

TABLE 1-continued

Chemical shifts in the $^1$H-NMR spectra of 3874 H3 and 3874 H1 recorded in deuteromethanol at 17° C.

| Position on C atom | 3874 H3 | 3874 H1 | Position on C atom | 3874 H3 | 3874 H1 |
|---|---|---|---|---|---|
| 16 | 2.00/1.24 | 1.99/1.24 | 42 | 2.68 | 2.98/2.92 |
| 17 | 4.25 | 4.25 | 43 | — | — |
| 18 | 1.99 | 1.99 | 44 | 6.10 | — |
| 18-CO | — | — | 45 | 7.23 | 7.75 |
| 19 | 4.38 | 4.39 | 46 | 6.26 | 6.62 |
| 20 | 2.24/1.68 | 2.24/1.67 | 47 | 6.28 | — |
| 21 | 4.37 | 4.38 | 48 | 1.87 | — |
| 22 | 6.10 | 6.10 | 1' | 4.53 | 4.54 |
| 23 | 6.17 | 6.17 | 2' | 3.85 | 3.88 |
| 24 | 6.50 | 6.49 | 3' | 2.71 | 2.80 |
| 25 | 6.35 | 6.35 | 4' | 3.12 | 3.17 |
| 26 | 6.50 | 6.49 | 5' | 3.21 | 3.23 |
| 27 | 6.79 | 6.79 | 5'-Me | 1.24 | 1.25 |
| 28 | 6.28 | 6.28 | | | |

It has furthermore been found that the compounds according to the invention have extremely strong fungicidal effects and, moreover, the activity covers a wide range of fungal genera and yeasts. Table 2 summarizes the minimum inhibitory concentrations of 3874 H1 and 3874 H3 by way of example.

TABLE 2

In vitro activity on dermatophytes, yeasts and molds (microdilution test in RPMI 1640 medium)

| STRAIN | Minimum inhibitory concentration MIC (µg/ml) | |
|---|---|---|
| | 3874 H1 | 3874 H3 |
| Dermatophytes | | |
| T. mentagrophytes 100/25 | 4 | 8 |
| T. rubrum 101/58 | 16 | 16 |
| E. floccosum 190/143 | 16 | 16 |
| Yeasts | | |
| C. albicans ATCC 90028 | 2 | 4 |
| C. albicans ATCC 90029 | 2 | 4 |
| C. glabrata ATCC 90030 | 4 | 4 |
| C. glabrata Berlin 12 | 2 | 4 |
| C. krusei 203/230 | 4 | 4 |
| C. krusei Berlin 1 | 2 | 2 |
| C. tropicalis 201/201 | 2 | 4 |
| C. tropicalis 201/202 | 2 | 4 |
| C. pseudotropicalis 202/218 | 2 | 4 |
| C. parapsilosis ATCC 90018 | 4 | 4 |
| C. neoformans ATCC 90112 | 2 | 2 |
| Molds | | |
| A. niger ATCC 16404 | 2 | 8 |
| A. fumigatus ATCC 9197 | 4 | 4 |
| A. flavus ATCC 9643 | 8 | 16 |

Incubation: 48 h at 35° C. (yeasts) or 6 days at 30° C. (dermatophytes and molds)

The superiority of the antibiotics according to the invention is shown particularly in so-called diffusion tests in which the compounds diffuse in an agar layer containing the test microbes. The diameter of the zones of inhibition is then a measure of the activity of the antibiotics (Table 3).

TABLE 3

Concentration-dependent zones of inhibition in mm caused by the antibiotics 3874 H1 and H3, compared with amphotericin B

| Concentration in mg/mL | 3874 H1 | 3874 H3 | Amphotericin B |
| --- | --- | --- | --- |
| 0.2 | 26 | 22 | 14 |
| 0.1 | 25 | 20 | 12 |
| 0.05 | 24 | 18 | 10 |
| 0.025 | 21 | 14 | 8 |
| 0.0125 | 19 | 13 | ø |
| 0.0063 | 17 | 12 | ø |

The effects of the compounds according to the invention exceed those of the commercial product amphotericin B considerably in some cases and therefore represent very valuable agents. The effect presumably derives from the ability of the novel heptaenes to bind ergosterol as heptaene/ergosterol complex. Ergosterol is an essential constituent of fungal plasma membranes. The complex formation alters the ergosterol in the membranes so that the structure of the plasma membrane is damaged and the fungal cell dies.

The membrane constituent corresponding to ergosterol in the cells of warm-blooded species is cholesterol. Many heptaenes disclosed in the literature bind cholesterol just as well as ergosterol and are therefore toxic compounds. The antibiotics 3874 H3 and 3874 H6, in particular, bind more strongly to ergosterol than to cholesterol and thus these compounds are particularly suitable for controlling fungal infections in humans and animals.

Besides the antimycotic effect, the antibiotics according to the invention have excellent inhibitory effects on protozoa such as, for example, Trichomonas species.

However, because of the cholesterol or sterol binding ability, the compounds 3874 H1 to H6 can also be employed in medicine whenever excessively high concentrations of steroids are unwanted. Examples thereof are reducing cholesterol levels in general or, specifically, treating benign prostate hypertrophies.

The present invention accordingly also relates to the use of the compounds according to the invention as pharmaceuticals, and to the use of the relevant compounds for producing pharmaceuticals for the treatment and/or prophylaxis of fungal infections and for the treatment of diseases associated with an increased steroid concentration.

The present invention furthermore relates to pharmaceuticals having a content of at least one compound according to the invention.

The pharmaceuticals according to the invention can be used enterally (orally), parenterally (intravenously), rectally or locally (topically). They can be administered in the form of solutions, powders, tablets, capsules (including microcapsules), ointments (creams or gels), liposome products, lipid complexes, colloidal dispersions or suppositories. Suitable ancillary substances for formulations of these types are the usual liquid or solid pharmaceutical bulking agents and extenders, solvents, emulsifiers, lubricants, masking flavors, dyes and/or buffer substances. An expedient dosage administered is 0.1–10, preferably 0.2–8, mg/kg of body weight. They are expediently administered in dose units which contain at least the effective daily amount of the compounds according to the invention, for example 30–3000, preferably 50–1000, mg.

The present invention is to be explained in detail by the following examples and by the contents of the claims.

EXAMPLE 1

Preparation of a Suspension of Spores of the Producer Strain 100 ml of nutrient solution (20 g of malt extract, 2 g of yeast extract, 10 g of glucose, 0.5 g of $(NH_4)_2HPO_4$ in 1 liter of tapwater, pH before sterilization: 6.0) in a 500 ml sterile Erlenmeyer flask are inoculated with the strain and incubated on a rotary shaker at 25° C. and 140 rpm for 72 hours. Subsequently, 120 ml of culture liquid are uniformly dispersed in a sterile 500 ml Erlenmeyer flask with the nutrient medium oatmeal infusion, 2.0 g/l, to which 15 g of agar/l have also been added for solidification, and decanted. The cultures are incubated at 25° C. for 10 to 14 days. The spores resulting after this time in one flask are rinsed out with 500 ml of deionized water which contains one drop of a commercial nonionic surfactant (for example TRITON X 100® supplied by Serva), and immediately used further or stored at −22° C. in 50% glycerol or at −140° C. in 10% dimethyl sulfoxide.

EXAMPLE 2

Preparation of a Culture or of a Preculture of the Producer Strain in an Erlenmeyer Flask A sterile 500 ml Erlenmeyer flask containing 100 ml of the nutrient solution described in Example 1 is inoculated with a culture grown in a slant tube or with 0.2 ml of spore suspension and incubated on a shaker at 140 rpm and 25° C. in the dark. Maximum production of the compounds according to the instant invention is reached after about 72 hours. A 72 hour-old submerged culture from the same nutrient solution suffices to inoculate 10 and 100 liter fermenters (inoculum about 5%).

EXAMPLE 3

Production of the Antibiotics 3874 H1–H6

A 10 liter fermenter is operated under the following conditions:

| Nutrient medium: | |
| --- | --- |
| Glucose | 15 g/l |
| Soybean meal | 15 g/l |
| Cornsteep | 5 g/l |
| $CaCO_3$ | 2 g/l |
| NaCl | 5 g/l |
| pH 7.0 | (before sterilization) |

Incubation time: 24 or 48 hours

Incubation temperature: 25° C.

Stirring speed: 200 rpm, with exclusion of light

Aeration: 5 liter of air/min.

Foam formation can be suppressed by repeated addition of a few drops of ethanolic polyol solution. Maximum production is reached after 48 hours.

EXAMPLE 4

Isolation of the Antibiotics 3874 H1 to H6

9 liter of the culture solution obtained as in Example 3 are centrifuged, and the biomass (~1.1 liter) is extracted by stirring twice with 2.2 liter of methanol each time. The combined extracts are concentrated in vacuo and dried, and the dry material is digested with diethyl ether. The residue which has been washed and delipidated in this way (41 g) is dissolved in 25% isopropanol/75% water and loaded onto a column which has a capacity of 3 liter and is packed with the MCl Gel® CHP20P adsorption resin. Column dimensions: width×height: 11.3 cm×30 cm. A solvent gradient from 25% isopropanol in water to 100% isopropanol is used for elution, and the outflow from the column is collected in 2 liter fractions.

The heptaene-containing fractions, which are checked by HPLC analyses, are collected and concentrated in vacuo, and freeze-dried (3.2 g).

EXAMPLE 5

High Pressure Liquid Chromatography (HPLC) of Heptaenes 3874 H1 to H6

Column: NUCLEOSIL® 100-5 $C_{18}AB$, 250/4.

Mobile Phase: 37.5% acetonitrile in 10 mM potassium phosphate buffer, pH 7.0

Flow rate: 1 ml per minute

Detection by UV absorption at 320 nm.

The retention times found for the individual components are as follows. The corresponding molecular weights $(M+H)^+$ determined by HPLC/mass spectrometry are also indicated. 10 mM ammonium acetate is used in place of phosphate buffer for the HPLC-MS.

| Retention time | Compound | $(M + H)^+$ |
| --- | --- | --- |
| 7.05 min | 3874 H1 | 1099.6 |
| 8.64 min | 3874 H4 | 1097.7 |
| 13.93 min | 3874 H2 | 1113.7 |
| 17.90 min | 3874 H5 | 1111.8 |
| 19.23 min | 3874 H3 | 1074.5 |
| 24.28 min | 3874 H6 | 1072.5 |

EXAMPLE 6

Enrichment of the 3874 H Components 2 g of the product obtained as in Example 4 are loaded onto a column which has a capacity of 3 liters and is packed with FRACTOGEL® TSK MW40 s (width×height=10 cm×50 cm). The mobile phase methanol is pumped through the column at a flow rate of 50 ml per minute, and the outflow from the column is collected in fractions (65 ml). Fractions 28 to 35 contain mainly the antibiotic 3874 H3 (after drying: 210 mg), fractions 39–43: H6 (9 mg), fractions 50–60: 3874 H1 and H2 (280 mg) and, finally, fractions 71 to 78: compounds 3874 H4 and H5 (17 mg).

EXAMPLE 7

Final Purification of 3874 H1, H2 and H3

The enriched antibiotics 3874 H1 and H2 (280 mg) and 3874 H3 (210 mg) obtained as in Example 6 are each fractionated on a NUCLEOSIL® $12C_{18}AB$ HPLC column (width×height=3.2 cm×25 cm) by the gradient method with 25% to 50% acetonitrile in water. The fractions were examined by HPLC (see Example 5) and combined appropriately, concentrated in vacuo and freeze-dried. They yielded 29 mg of 3874 H1 in 95% purity,
11 mg of 3874 H2 in 94% purity,
65 mg of 3874 H3 in 97% purity.

EXAMPLE 8

Final Purification by Preparative HPLC in the Phosphate Buffer/Isopropanol System Process as in Example 7 but using 10 mM potassium phosphate buffer, pH 7, and isopropanol as mobile phase. Desalting of the separated components as in Example 7.

38 mg of 3874 H1 in 97% purity,
21 mg of 3874 H2 in 96% purity,
83 mg of 3874 H3 in 98% purity.

What is claimed is:

1. A compound 3874 H1, H2, H3, H4, H5 or H6 with the following formula

3874 H1, molecular formula: $C_{58}H_{86}N_2O_{18}$, MW 1099.3,

3874 H2, molecular formula: $C_{59}H_{88}N_2O_{18}$, MW 1113.3,

3874 H3, molecular formula: $C_{57}H_{87}NO_{18}$, MW 1074.3, or physiologically tolerated salts thereof or chemical equivalents thereof.

2. A compound as claimed in claim 1, which can be prepared by fermenting the microorganism DSM 11007 or one of its variants or mutants under suitable conditions, isolating one or more of the compounds 3874 H1 to H6, and converting them where appropriate to their salts or chemical equivalents.

3. A pharmaceutical composition comprising an effective amount of at least one compound as claimed in claim 1.

4. A method for the treatment of fungal diseases which comprises administering to a host in need of such treatment, a pharmaceutical composition as claimed in claim 3.

5. A method for the treatment of fungal diseases which comprises administering to a host in need of such treatment, an effective amount of a compound as claimed in claim 1.

6. A method for the treatment of trichomonad diseases which comprises administering to a host in need of such treatment, a pharmaceutical composition as claimed in claim 3.

7. A method for the treatment of trichomonad diseases which comprises administering to a host in need of such treatment, an effective amount of a compound as claimed in claim 1.

8. A process for producing a pharmaceutical composition comprising an effective amount of at least one compound as claimed in claim 1, which comprises converting at least one compound as claimed in claim 1 with suitable ancillary substances and/or excipients into a suitable dosage form.

* * * * *